United States Patent
Cruse

(10) Patent No.: US 6,932,988 B2
(45) Date of Patent: Aug. 23, 2005

(54) KIT AND METHOD FOR MIGRAINE HEADACHE TREATMENT

(76) Inventor: Suzanne Cruse, 819 NE. 8th St., N. Bend, WA (US) 98045

( * ) Notice: Subject to any disclaimer, the term of this patent is extended or adjusted under 35 U.S.C. 154(b) by 79 days.

(21) Appl. No.: 10/662,246

(22) Filed: Sep. 15, 2003

(65) Prior Publication Data

US 2004/0058019 A1 Mar. 25, 2004

Related U.S. Application Data

(60) Provisional application No. 60/411,059, filed on Sep. 16, 2002.

(51) Int. Cl.[7] .......................... A61K 35/78; A61K 31/60
(52) U.S. Cl. ...................... 424/725; 424/765; 514/165; 435/975
(58) Field of Search .................. 424/725, 765; 514/165; 435/975

(56) References Cited

U.S. PATENT DOCUMENTS

| | | | | |
|---|---|---|---|---|
| 3,113,028 A | * | 12/1963 | Cooper et al. ........... | 426/330.3 |
| 4,003,999 A | * | 1/1977 | Lybrand et al. ............ | 424/729 |
| 4,046,917 A | | 9/1977 | Scholtysik .................. | 424/326 |
| 4,916,125 A | | 4/1990 | Herrling et al. .............. | 514/89 |
| 5,273,759 A | | 12/1993 | Simmons .................... | 424/465 |
| 5,538,959 A | | 7/1996 | Mauskop .................... | 514/165 |
| 5,895,672 A | * | 4/1999 | Cooper ....................... | 426/79 |
| 5,914,129 A | | 6/1999 | Mauskop .................... | 424/464 |
| 5,939,076 A | | 8/1999 | Allocca ....................... | 424/400 |
| 5,972,916 A | | 10/1999 | Armellino et al. .......... | 514/165 |
| 6,043,244 A | | 3/2000 | Caruso ........................ | 514/250 |
| 6,106,837 A | | 8/2000 | Hirsch ...................... | 424/195.1 |
| 2004/0255788 A1 | * | 12/2004 | Bowe .......................... | 99/279 |

* cited by examiner

Primary Examiner—Christopher R. Tate
(74) Attorney, Agent, or Firm—Dean A. Craine

(57) ABSTRACT

A kit and method for treating migraine headaches comprising the preparing of an oral composition containing at least two bags of black pekoe tea brewed in approximately three ounces of boiling water for ten to thirty seconds. After brewing, the bags of tea are removed and two 325 mg aspirin tablets, one to two teaspoonfuls or tablets of apple cider vinegar, and one to three teaspoonfuls of honey are mixed into the brewed tea. The entire hot and concentrated composition is then cooled over ice so that a person suffering from a migraine headache may quickly drink it.

2 Claims, 1 Drawing Sheet

KIT AND METHOD FOR MIGRAINE HEADACHE TREATMENT

This is a utility patent application which claims benefit of U.S. Provisional Application No. 60/411,059 filed on Sep. 16, 2002.

BACKGROUND OF THE INVENTION

1. Field of the Invention

This invention relates to compositions and methods for treating migraine headaches and, more particularly, to compositions and methods used to quickly alleviate the symptoms using safe, readily available ingredients.

2. Description of the Related Art

Migraine headaches affect millions of people and are the most severe and intensive type of headaches. The physically debilitating symptoms, which may last from two hours to two days, include throbbing pain on one side of the head, nausea, blurring vision, and sensitivity to light, sounds, and smells.

The goal for treating migraine headaches is to relieve all of the symptoms quickly and safely and without harmful side effects.

Conventional medical treatments for migraines use pharmacological agents to prevent headaches and reduce symptoms. Examples of conventional treatments include vasodilating drugs such as ergotamines, calcium blockers, analgesics such as aspirin and acetaminophen, and anti-nausea drugs, such as promethazine. A wide variety of non-conventional treatments are used, including the ingestion of herbal solutions and teas, aromatherapy, biofeedback, and acupuncture.

It is widely know that perenteral medications have a faster onset of action than oral medications. Unfortunately, administration of perenteral medications is not an option for non-medical trained individuals.

Ideally, what is needed is a safe and effective oral composition and method of treating migraine headaches that relieves all of its symptoms, is easy to prepare, and has a relatively fast onset of action.

SUMMARY OF THE INVENTION

It is an object of the present invention to provide a safe and effective oral composition and method of treating migraine headaches.

It is another object of the present invention to provide a composition and method of treating migraine headaches that relieves all of the common symptoms.

It is a further object of the present invention to provide such a composition and method that is easy to prepare, used orally, and has a relatively fast onset of action.

These and other objects of the present invention are met by the kit and method of treating migraine headaches disclosed herein that comprises using the items in the kit to easily and quickly prepare a liquid composition that is drunk when the onset of a migraine occurs. The kit includes an outer carrying container that includes one to two teaspoons or tablets of apple cider vinegar, three bags of black pekoe tea, two aspirin tablets, and, one to two tablespoons of honey.

At the onset of a migraine headache, three ounces of water is heated for brewing tea. The three tea bags are removed from the carrying container and placed into the hot water for ten to thirty seconds. The tea bags are removed and the other three ingredients are then added and mixed into the tea. The entire composition is then poured over a glass filled with four to six ounces of ice to quickly chill the composition for rapid consumption. The entire composition is then rapidly drunk.

DESCRIPTION OF THE PREFERRED EMBODIMENT(S)

Figure 1:
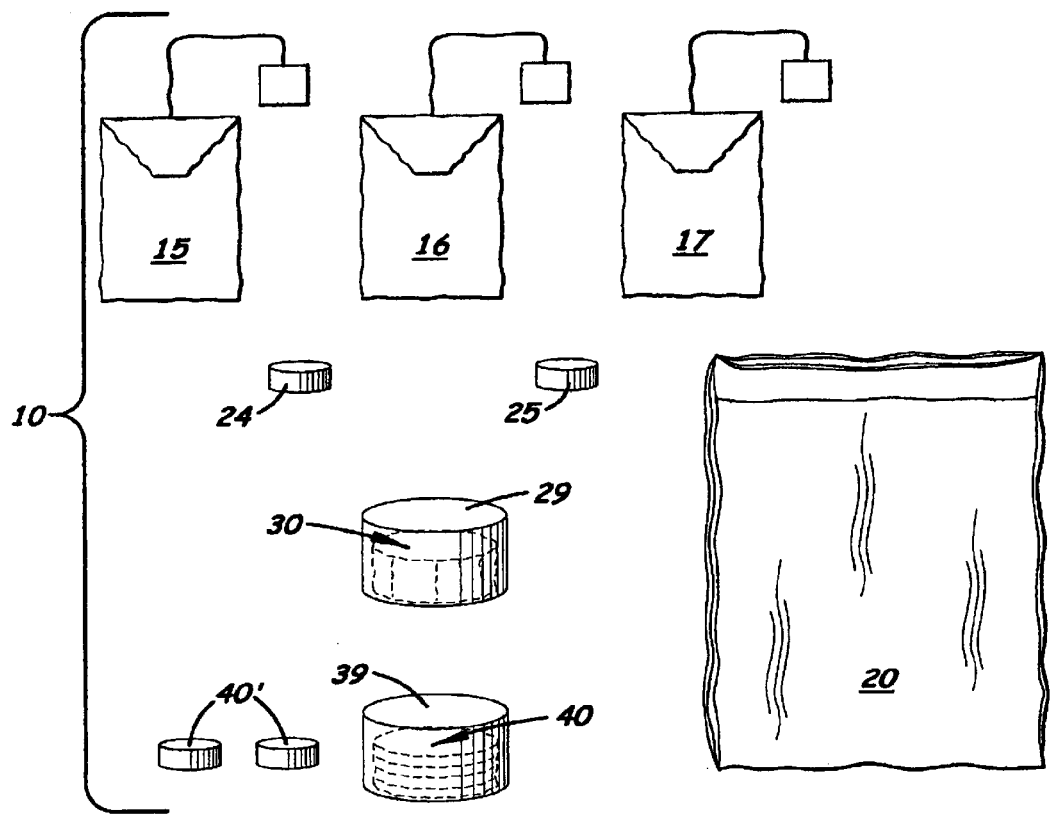
FIG. 1 is an illustration of the kit for treating a migraine headache.
Figure 2:
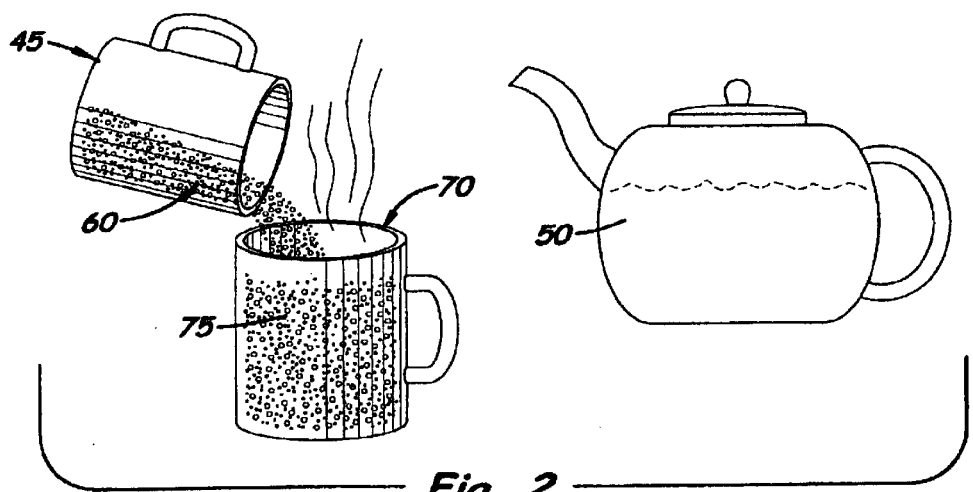
FIG. 2 is an illustration showing the hot composition being poured into a cup filled with ice.

Shown in the accompanying FIGS. is a kit 10 comprising a shipping container 20 containing three bags of black pekoe tea 15, 16, 17, a first leak-proof container 29 holding one to two teaspoons (5–10 mls) of apple cider vinegar 30, two 325 mg aspirin tablets 24, 25 and a second leak proof container 39 containing one to three teaspoons (5–15 mls) of honey 40.

At the onset of a migraine headache, at least three ounces of hot water is prepared. The water is made sufficiently hot for brewing tea. After heating, the three ounces of hot water is then poured into a suitable cup 45. The two to three tea bags 15, 16, 17 are then removed from the shipping container 20 and steeped in the cup 45 for ten to thirty seconds. The tea bags 15, 16, 17 are removed from the cup 45 and the two aspirin tablets 24, 25, one to two teaspoonfuls of apple cider vinegar 30 and one to three teaspoonfuls of honey 40 are then added and mixed thoroughly to form a hot concentrated composition. The entire composition 60 is then poured over a second glass or cup 70 filled with four to six ounces of ice 75 to dilute the composition and to quickly chill the liquid composition 60 for rapid consumption. The chilled, diluted composition 60 is then rapidly drunk.

It is postulated that the tea bags 15, 16, 17 provide a relatively high dose of caffeine and tannins. The aspirin tablets 24, 25 act as an analgesic, while the honey 40 serves as a source of calcium which is believed to cause vasoconstriction. The apple cider vinegar 30 contains acetic acid which lowers the pH in the stomach and improves absorption of the caffeine, tannins, aspirin, and calcium. The apple cider vinegar 30 could be in tablet form (1 tablet equals 1 teaspoon of apple cider vinegar).

Also disclosed herein is a method for treating migraine headaches comprising the following steps:

a. selecting a kit 10 containing at least three bags of black pekoe tea 15, 16, 17, two 325 mg aspirin tablets 24, 25, at least one teaspoon (5 mls) or tablet of apple cider vinegar 30, and at least one teaspoon (5 mls) of honey 40;

b. heating at least two ounces of water until sufficiently hot for brewing tea bags;

c. brewing at least two said bags of black pekoe tea 15, 16 in said hot water 50;

d. removing said bags of black pekoe tea 15, 16 from said hot water 50;

e. adding said aspirin tablets 24, 25, said apple cider vinegar 30, and at least one teaspoon of said honey 40 to said hot water 50 to create a concentrated composition 60;

f. selecting a cup 70 containing two to six ounces of ice 75;

g. pouring said concentrated composition 60 into said cup 70 to dilute and cool said concentrated composition 60 for rapid drinking; and, h. rapidly drinking said concentrated composition 60.

The main advantage of the kit 10 is its portability and the convenience of having all of the ingredients on hand for effectively treating a migraine headache. The entire concentrated composition can be made quickly and without error by the migraine sufferer.

In compliance with the statute, the invention described herein has been described in language more or less specific as to structural features. It should be understood, however, that the invention is not limited to the specific features shown, since the means and construction shown, is comprised only of the preferred embodiments for putting the invention into effect. The invention is therefore claimed in any of its forms or modifications within the legitimate and valid scope of the amended claims, appropriately interpreted in accordance with the doctrine of equivalents.

I claim:

1. A migraine treatment kit, comprising the following agents housed therein:
   a. at least two bags of black pekoe tea;
   b. two 325 mg aspirin tablets;
   c. at least one teaspoonful of apple cider vinegar within a first container; and,
   d. at least one teaspoonful of honey within a first container.

2. A method for migraine headache treatment comprising:
   a. selecting a kit 10 containing at least three bags of black pekoe tea 15, 16, 17, two 325 mg aspirin tablets 24, 25, at least one teaspoon (5 mls) or tablet of apple cider vinegar 30, and at least one teaspoon (5 mls) of honey 40;
   b. heating at least two ounces of water until sufficiently hot for brewing tea bags;
   c. brewing at least two said bags of black pekoe tea 15, 16 in said hot water 50;
   d. removing said bags of black pekoe tea 15, 16 from said hot water 50;
   e. adding said aspirin tablets 24, 25, said apple cider vinegar 30, and said honey 40 to said hot water 50 to form a concentrated composition 60;
   f. selecting a cup 70 with two to six ounces of ice 75;
   g. pouring said concentrated composition 60 into said cup 70 to dilute and cool said concentrated composition 60 for rapid drinking; and,
   h. rapidly drinking said composition 60.

\* \* \* \* \*